US009755393B2

United States Patent
Vogler et al.

(10) Patent No.: US 9,755,393 B2
(45) Date of Patent: Sep. 5, 2017

(54) CONTROLLING A LASER SOURCE TO COMPENSATE FOR CHANGE IN PULSE LENGTH BY ADJUSTING CYCLE NUMBER OF AN AMPLIFIER

(71) Applicant: WAVELIGHT GMBH, Erlangen (DE)

(72) Inventors: Klaus Vogler, Eckental (DE); Olaf Kittelmann, Berlin (DE); Matthias Foesel, Drosendorf (DE); Christof Donitzky, Eckental (DE)

(73) Assignee: Wavelight GmbH (DE)

( * ) Notice: Subject to any disclaimer, the term of this patent is extended or adjusted under 35 U.S.C. 154(b) by 75 days.

(21) Appl. No.: 14/369,824

(22) PCT Filed: Nov. 14, 2012

(86) PCT No.: PCT/EP2012/072567
§ 371 (c)(1),
(2) Date: Jun. 30, 2014

(87) PCT Pub. No.: WO2014/075713
PCT Pub. Date: May 22, 2014

(65) Prior Publication Data
US 2014/0361145 A1  Dec. 11, 2014

(30) Foreign Application Priority Data

Nov. 14, 2012  (WO) ............... PCT/EP2012/072567

(51) Int. Cl.
*H01S 3/00*  (2006.01)
*A61F 9/008*  (2006.01)
(Continued)

(52) U.S. Cl.
CPC ............ *H01S 3/0057* (2013.01); *A61F 9/008* (2013.01); *A61F 9/0084* (2013.01); *G01J 11/00* (2013.01); *H01S 3/106* (2013.01)

(58) Field of Classification Search
CPC ........ G01J 11/00; G01J 1/0411; G01J 1/0448; G01J 2001/4238; G01J 1/16; A61F 9/008;
(Continued)

(56) References Cited

U.S. PATENT DOCUMENTS 9,000,403 B2 * 4/2015 Crouch ................. H05G 2/008
250/504 R
2005/0226287 A1  10/2005 Shah et al.
(Continued)

FOREIGN PATENT DOCUMENTS

JP    2011-520561      7/2011
RU       101277 U1    1/2011
WO    2009117451 A1   9/2009

OTHER PUBLICATIONS

Geskus; "Design and construction of regenerative amplifier and compressor for chirped pulse amplification"; Retrieved from the internet: URL:http:/lpno.tnw.utwente.nl/publications/Msc/MSc_Geskus_20060611.pdf.
(Continued)

*Primary Examiner* — Que T Le
*Assistant Examiner* — Jennifer Bennett

(57) ABSTRACT

In certain embodiments, a system (10) comprises a laser source (20), one or more optical elements (24), a monitoring device (28), and a control computer (30). The laser source (20) emits one or more laser pulses. The optical elements (24) change a pulse length of the laser pulses, and the monitoring device (28) measures the pulse length of the laser pulses to detect the change in the pulse length. The control computer (30) receives the measured pulse length from the monitoring device (28), determines one or more laser parameters that compensate for the change in the pulse length, and controls the laser source (20) according to the laser parameters.

12 Claims, 3 Drawing Sheets

(51) Int. Cl.
*G01J 11/00* (2006.01)
*H01S 3/106* (2006.01)

(58) Field of Classification Search
CPC ...... A61F 9/0084; H01S 3/106; H01S 3/0057; H01S 3/005; G01B 11/272
USPC ..... 250/201.1, 206, 216, 214 R, 205, 504 R; 356/218, 5.01; 348/78; 359/276, 337.5, 359/333; 372/30, 29.011
See application file for complete search history.

(56) References Cited

U.S. PATENT DOCUMENTS

| | | | |
|---|---|---|---|
| 2008/0112709 A1 | 5/2008 | Oulianov et al. | |
| 2008/0259445 A1* | 10/2008 | Kubo | G02B 21/0032 359/388 |
| 2009/0274181 A1* | 11/2009 | Akahane | H01S 3/2308 372/25 |
| 2011/0182306 A1* | 7/2011 | Hosseini | B23K 26/0624 372/25 |

OTHER PUBLICATIONS

Helguera, M.; "An Introuction to Ultrasound"; [Retrieved from internet on Jan. 23, 2017]<URL:http://web.archive.org/web/20100710221442/http://www.cis.rit.edu/research/ultrasound/ultrasoundintro/ultraintro.html> and published on Jul. 10, 2010 as per Wayback Machine.

* cited by examiner

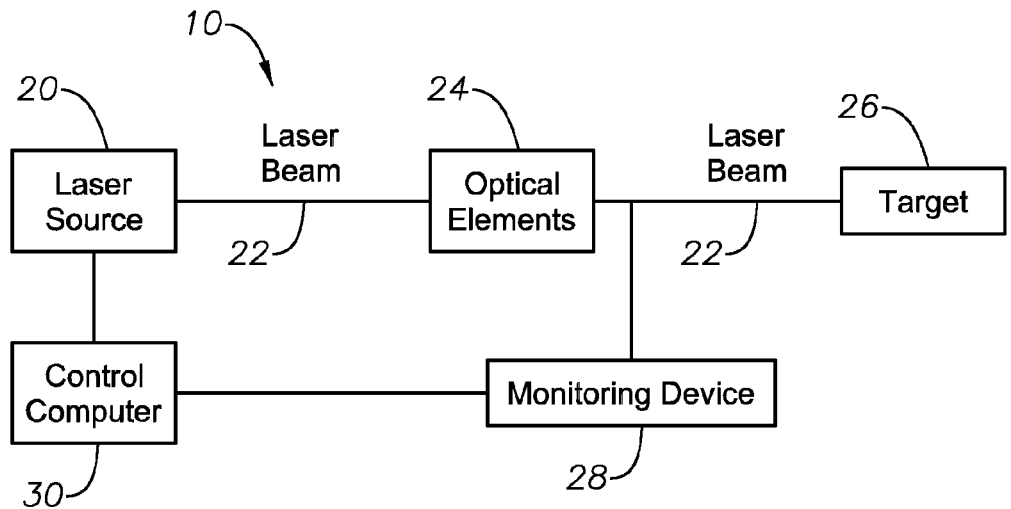
FIG. 1
FIG. 2A
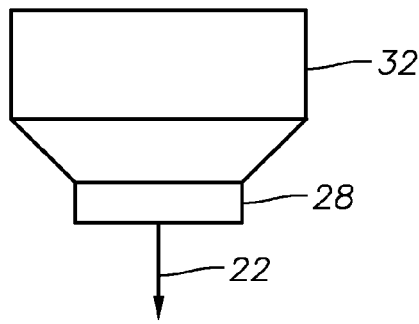
FIG. 2B
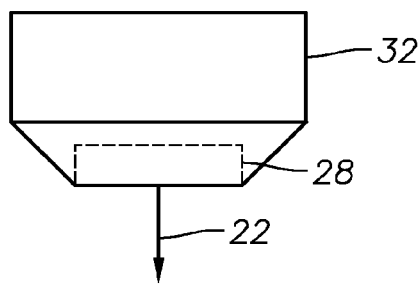

CONTROLLING A LASER SOURCE TO COMPENSATE FOR CHANGE IN PULSE LENGTH BY ADJUSTING CYCLE NUMBER OF AN AMPLIFIER

CROSS REFERENCE TO RELATED APPLICATIONS

This application is a section 371 national stage phase of International Application No. PCT/EP2012/072567, filed 14 Nov. 2012, titled "LASER PULSE FOCUSING," which is hereby incorporated by reference in its entirety.

TECHNICAL FIELD

The present disclosure relates generally to laser systems, and more particularly to laser pulse focusing.

BACKGROUND

Ultrashort laser pulses are routinely used to process materials in medicine and science. In certain cases, very high peak intensities may be required. In certain applications, the laser pulses pass through optics and are then focused at a focus point at a target. The optics, however, may stretch the laser pulses with respect to time, which reduces the peak intensity of the pulses at the target. Moreover, shorter laser pulses may experience greater stretching than longer laser pulses.

BRIEF SUMMARY

In certain embodiments, a system comprises a laser source, one or more optical elements, a monitoring device, and a control computer. The laser source emits one or more laser pulses. The optical elements change a pulse length of the laser pulses, and the monitoring device measures the pulse length of the laser pulses to detect the change in the pulse length. The control computer receives the measured pulse length from the monitoring device, determines one or more laser parameters that compensate for the change in the pulse length, and controls the laser source according to the laser parameters.

In certain embodiments, a method comprises: emitting, by a laser source, one or more laser pulses; changing, by one or more optical elements, a pulse length of the laser pulses; measuring, by a monitoring device, the pulse length of the laser pulses to detect the change in the pulse length; receiving, at a control computer, the measured pulse length from the monitoring device; determining, by the control computer, one or more laser parameters that compensate for the change in the pulse length; and controlling, by the control computer, the laser source according to the laser parameters.

BRIEF DESCRIPTION OF THE DRAWINGS

Exemplary embodiments of the present disclosure will now be described by way of example in greater detail with reference to the attached figures, in which:

FIG. 1 illustrates an example of a system configured to focus laser pulses on a target according to certain embodiments;

FIGS. 2A and B illustrate examples of a focusing objective and a monitoring device that may be used with the system of FIG. 1 according to certain embodiments;

DESCRIPTION OF EXAMPLE EMBODIMENTS

Figure 3:
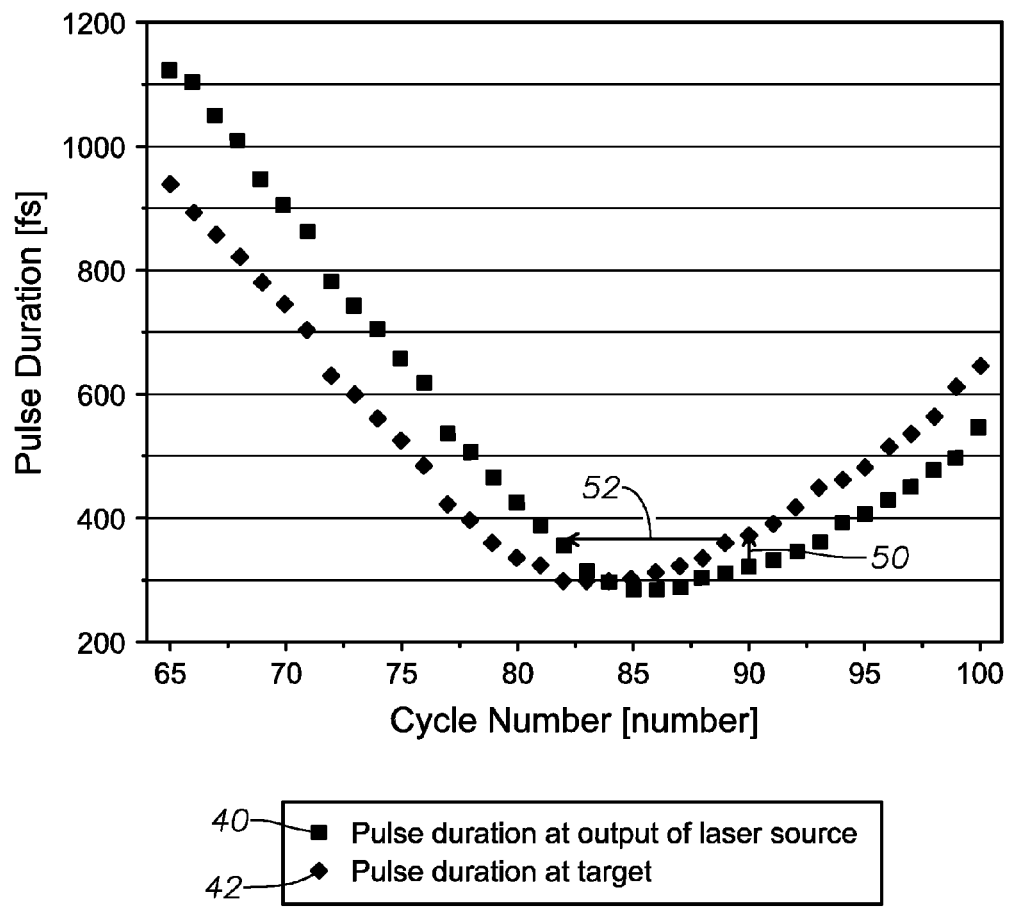
FIG. 3 illustrates an example of cycle numbers affecting pulse duration.

Referring now to the description and drawings, example embodiments of the disclosed apparatuses, systems, and methods are shown in detail. The description and drawings are not intended to be exhaustive or otherwise limit or restrict the claims to the specific embodiments shown in the drawings and disclosed in the description. Although the drawings represent possible embodiments, the drawings are not necessarily to scale and certain features may be exaggerated, removed, or partially sectioned to better illustrate the embodiments.

FIG. 1 illustrates an example of a system 10 configured to focus laser pulses of a laser beam 22 on a target 26 according to certain embodiments. In the example, system 10 includes a laser source 20, one or more optical elements 24, a monitoring device 28, and a control computer 30. In certain embodiments, monitoring device 28 measures the pulse length of the laser pulses output from optical elements 24 to detect changes (e.g., increases or decreases) in the pulse length and sends the measurement information to control computer 30. Control computer 30 and/or laser source 20 compensate for the changes in pulse length. In certain embodiments, control computer 30 determines laser source parameters that may compensate for the changes (e.g., pulse length changes) and then controls laser source 20 using the parameters to direct laser beam 22 towards target 26.

In certain embodiments, optical elements 24 and/or laser source 20 may yield pulse length changes. In the embodiments, elements (such as optical elements) of the laser source 20 may be used to apply the appropriate adjustment (such as a negative chirp) to compensate for the dispersion (such as positive dispersion) of the optical elements 24 and/or laser source 20 that cause a chirp (such as a positive chirp). Alternatively, a positive chirp may be applied to compensate for a negative dispersion of optical elements 24 and/or laser source 20 that cause a negative chirp. System 10 may output to target 26 laser pulses with a desired pulse length and pulse energy. In certain cases, the pulse length may be minimized.

Laser source 20 generates and emits a laser beam with ultrashort laser pulses. In this document, an "ultrashort" pulse of light refers to a light pulse that has a duration that is less than or equal to a nanosecond, such as on the order of a nanosecond, picosecond, femtosecond, or attosecond. Examples of laser source 20 include nanosecond, femtosecond, picosecond, and attosecond lasers. The laser beam may have any suitable wavelength, such as a wavelength in the range of 300 to 1900 nanometers (nm), for example, a wavelength in the range of 300 to 650, 650 to 1050, 1050 to 1250, or 1100 to 1900 nm. The laser beam may comprise pulses of any suitable pulse duration, such as 1 to 1000 femtoseconds (fs), e.g., approximately 10 fs.

Optical elements 24 may comprise one or more elements that can operate on light, e.g., reflect, refract, diffract, and/or transmit light. Optical elements 24 may include any suitable elements, such as a focusing objective that can focus laser beam 22 onto target 26. Optical elements 24 may change, e.g., increase or decrease, the pulse length of laser pulses. In certain embodiments, optical elements 24 may apply a positive dispersion that stretches the pulses in time. For example, optical elements 24 may increase the pulse length from 10 fs to 200 fs. Moreover, shorter (e.g., 200 fs or less)

laser pulses may experience greater stretching than longer (e.g., approximately 400 fs) laser pulses.

Monitoring device 28 measures the pulse length of laser pulses to detect pulse stretching with respect to time and then sends the measurement information to control computer 30. The pulse length may be measured in any suitable manner. In certain embodiments, monitoring device 28 uses a nonlinear measurement technique in which a pulse is copied and the copies are combined in a nonlinear medium. The nonlinear medium produces a particular signal only when both pulse copies are present at the same time, so varying the delay between the pulse copies and measuring the signal for each delay gives an estimate of the pulse length. These monitoring devices may include an SHG crystal, a photodiode, and/or a multi-photon detector that detects two or more photons. Examples of these monitoring devices include frequency-resolved optical gating (FROG) devices, autocorrelation monitors, and solar blind detectors (for multi-photon absorption of near infra red laser pulses).

Control computer 30 is configured to receive the measured pulse length from the monitoring device 28, determine one or more laser parameters that substantially compensate for the stretching of the pulse length in time, and control laser source 20 according to the laser parameters. The laser parameters and/or laser source elements may compensate for the change of pulse width in any suitable manner. For example, the laser source elements may generate a negative chirp to compensate for a positive dispersion that optical elements 24 apply to the laser pulses (or vice versa). As another example, the parameters may increase the cycle number of a regenerative amplifier of laser source 20 to induce a phase modulation to apply a negative chirp.

In certain examples, the positive dispersion, or group-velocity delay (GVD), applied by optical elements 24 may be expressed as $GVD_{pos}$. The negative chirp applied by the laser parameters may be expressed as $|GVD_{neg}|=|GVD_{pos}|$. The negative chirp may have any suitable value, e.g., a value in the range of less than 0 femtoseconds$^2$ (fs$^2$) to greater than $-20,000$ fs$^2$. In certain embodiments, laser source 20 may perform the full compensation to substantially compensate for the pulse length changes. In other embodiments, laser source 20 may perform a partial compensation that does not substantially compensate for the pulse length changes, and another device may perform the rest of the compensation prior to outputting the pulses to the target 26.

Target 26 may represent any suitable material, such as living or non-living biological tissue. In certain embodiments, target 26 is tissue of the eye, such as corneal tissue. The focus point of the laser beam may create a laser-induced optical breakdown (LIOB) at target 26. The minimized pulse length may yield a LIOB at a lower pulse energy, which may reduce or avoid undesired effects, such as scattered radiation, gas bubbles, or opaque bubble layers.

FIGS. 2A and B illustrate examples of a focusing objective 32 and a monitoring device 28 that may be used with system 10. Focusing objective 32 is an optical element 24 and may be any suitable optical element that can focus laser beam 22, such as an F-theta objective. In certain embodiments, focusing objective 32 may be an ablation cone.

Monitoring device 28 may measure the pulse length at any suitable location where the measurement can provide control computer 30 with information that can allow control computer 30 to calculate laser parameters that can substantially compensate for the change in pulse width. In the example, monitoring device 28 measures the pulse length of pulses that are output at the outlet of focusing objective 32. Monitoring device 28 may be coupled to focusing objective 32 (as shown as an example in FIG. 2A) or disposed within focusing objective 32 (as shown as an example in FIG. 2B).

Monitoring device 28 may measure the pulse length at any suitable time, such as whenever calibration is desired. In certain cases, the measurement may be performed mechanically or automatically, such as periodically (e.g., weekly, daily, or hourly) or in response to a trigger event (e.g., when system 10 is turned on or when new patient information is entered). In other cases, the measurement may be performed in response to a user request, which may be made by any suitable user, e.g., by a surgeon, a service person, or a manufacturer.

FIG. 3 illustrates an example of a graph that shows the relationship between cycle numbers and pulse duration. In the graph, pulse duration 40 is the pulse duration at the output of laser source 20, and pulse duration 42 is the pulse duration at target 26. Reference arrow 50 indicates an increase in pulse duration from the pulse duration 40 at the output of laser source 20 to the pulse duration 42 at target 26. Reference arrow 52 indicates a change in cycle number from 90 cycles to 83-85 cycles to yield a pulse duration 42 that is closer to the minimal pulse duration 40 of pulse in the optical system.

Figure 4:
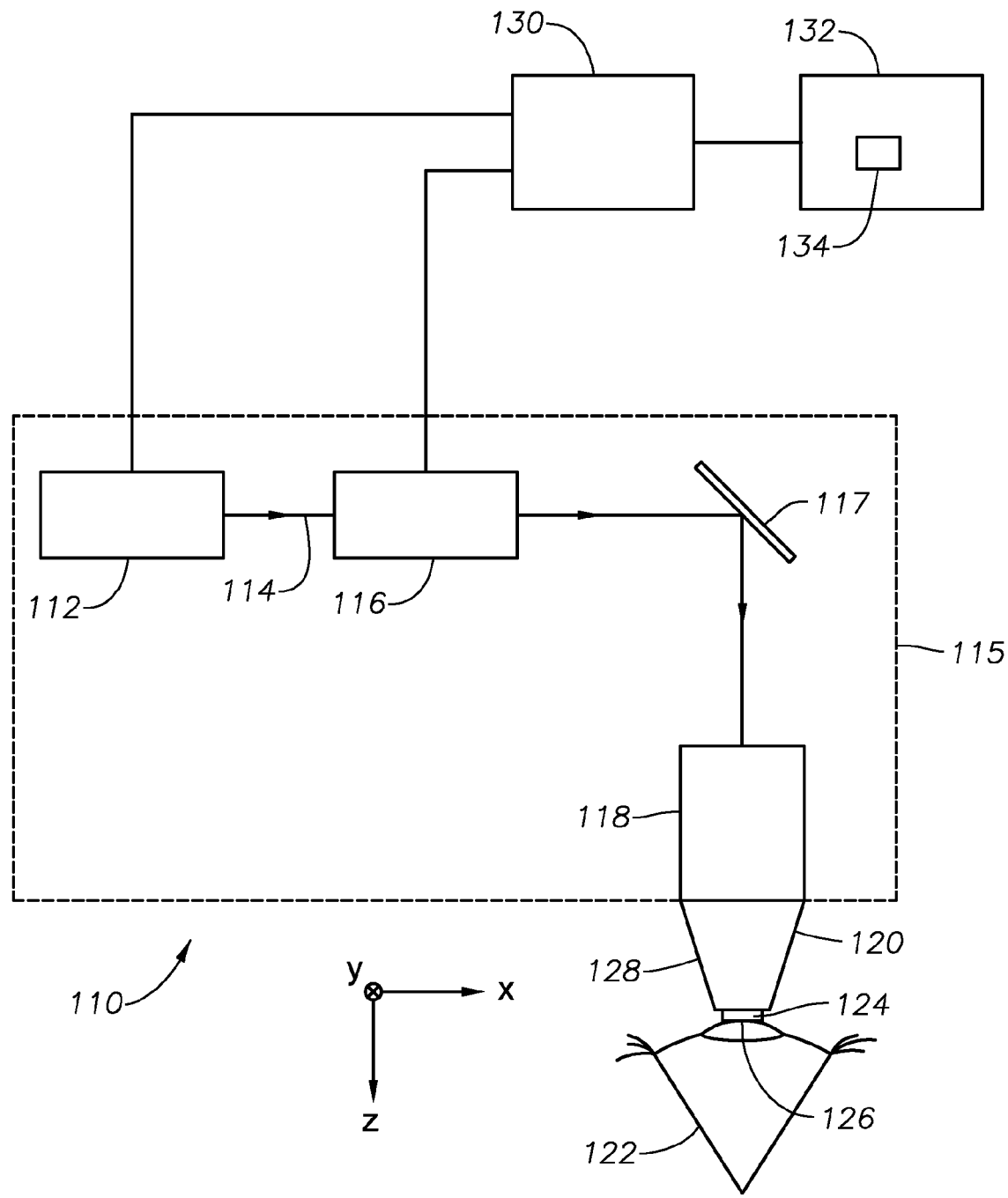
FIG. 4 illustrates an example of a device with which the system of FIG. 1 may be used according to certain embodiments.

FIG. 4 illustrates an example of a device 110 with which system 10 of FIG. 1 may be used according to certain embodiments. System 10 may be used for any suitable laser application. Examples of applications include scientific and medical applications, such as surgical or diagnostic applications. For example, system 10 may be used with a laser surgical system, such as the one described below, a multiphoton spectroscopy, or other diagnostic system.

In certain embodiments, device 110 performs laser refractive surgery on an eye 122. The device 110 includes a laser device 115, a patient adapter 120, a control computer 130, and a memory 132 coupled as shown in the example. The laser device 115 may include a laser source 112, a scanner 116, one or more optical elements 117, and/or a focusing objective 118 coupled as shown in the example. The patient adapter 120 may include a contact element 124 (which has an abutment face 126 disposed outwardly from a sample) and a sleeve 128 coupled as shown. The memory 132 stores a control program 134.

Laser source 112 may be similar to laser source 20 of FIG. 1, and optical elements 117 and focusing objective 118 may be similar to optical elements 24. The scanner 116, optical elements 117, and focusing objective 118 are in the beam path and may be readily removed from beam path depending on the application. The scanner 116 transversely (x and y directions) and longitudinally (z direction) controls the focal point of a laser beam 114. One (or more) optical elements 117 direct the laser beam 114 towards the focusing objective 118. The focusing objective 118 focuses the laser beam 114 onto the patient adapter 120, and may be separably coupled to the patient adapter 120. Patient adapter 120 interfaces with the cornea of the eye 122. In the example, the patient adapter 120 has a sleeve 128 coupled to a contact element 124. The sleeve 128 couples to the focusing objective 118.

The control computer 130 controls controllable components, e.g., the laser source 112, scanner 116, and/or at least one optical element 117, in accordance with the control program 134. The control program 134 contains computer code that instructs the controllable components to focus the pulsed laser radiation at a region of the cornea to photodisrupt at least a portion of the region.

A component of the systems and apparatuses disclosed herein (such as control computer 130) may include an interface, logic, memory, and/or other suitable element, any of which may include hardware and/or software. An interface can receive input, send output, process the input and/or output, and/or perform other suitable operations. Logic can perform the operations of a component, for example, execute instructions to generate output from input. Logic may be encoded in memory and may perform operations when executed by a computer. Logic may be a processor, such as one or more computers, one or more microprocessors, one or more applications, and/or other logic. A memory can store information and may comprise one or more tangible, computer-readable, and/or computer-executable storage medium. Examples of memory include computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server), and/or other computer-readable media.

In particular embodiments, operations of the embodiments may be performed by one or more computer readable media encoded with a computer program, software, computer executable instructions, and/or instructions capable of being executed by a computer. In particular embodiments, the operations may be performed by one or more computer readable media storing, embodied with, and/or encoded with a computer program and/or having a stored and/or an encoded computer program. Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

Other modifications are possible without departing from the scope of the invention. For example, the description illustrates embodiments in particular practical applications, yet other applications will be apparent to those skilled in the art. In addition, future developments will occur in the arts discussed herein, and the disclosed systems, apparatuses, and methods will be utilized with such future developments.

The scope of the invention should not be determined with reference to the description. In accordance with patent statutes, the description explains and illustrates the principles and modes of operation of the invention using exemplary embodiments. The description enables others skilled in the art to utilize the systems, apparatuses, and methods in various embodiments and with various modifications, but should not be used to determine the scope of the invention.

The scope of the invention should be determined with reference to the claims and the full scope of equivalents to which the claims are entitled. All claims terms should be given their broadest reasonable constructions and their ordinary meanings as understood by those skilled in the art, unless an explicit indication to the contrary is made herein. For example, use of the singular articles such as "a," "the," etc. should be read to recite one or more of the indicated elements, unless a claim recites an explicit limitation to the contrary. As another example, "each" refers to each member of a set or each member of a subset of a set, where a set may include zero, one, or more than one element. In sum, the invention is capable of modification, and the scope of the invention should be determined, not with reference to the description, but with reference to the claims and their full scope of equivalents.

What is claimed is:

1. A system comprising:
    a laser source configured to emit one or more laser pulses, the laser source comprising an amplifier;
    one or more optical elements that change a pulse length of the one or more laser pulses, the one or more optical elements comprising a focusing objective;
    a monitoring device configured to measure the pulse length of the one or more laser pulses to detect the change in the pulse length, the monitoring device coupled to or disposed within the focusing objective; and
    a control computer configured to:
        receive the measured pulse length from the monitoring device;
        determine one or more laser parameters that compensate for the change in the pulse length, the one or more laser parameters comprising a cycle number of the amplifier; and
        control the laser source according to the one or more laser parameters by instructing the laser source to adjust the cycle number to compensate for the detected change in the pulse length.

2. The system of claim 1, wherein the change in the pulse length is an increase or decrease in pulse length.

3. The system of claim 1, wherein the control computer is configured to determine the one or more laser parameters by determining one or more parameters that introduce a positive or negative chirp to compensate for the change in pulse length.

4. The system of claim 1, wherein:
    the one or more optical elements change the pulse length by causing a negative chirp in the laser pulses; and
    the control computer is configured to determine the one or more laser parameters by determining one or more parameters that introduce a positive or negative chirp to compensate for the change in the pulse length.

5. The system of claim 1, the one or more laser parameters substantially compensate for the change in pulse length.

6. The system of claim 1, the one or more laser parameters partially compensate for the change in pulse length.

7. A method comprising:
    emitting, by a laser source, one or more laser pulses, the laser source comprising an amplifier;
    changing, by one or more optical elements, a pulse length of the one or more laser pulses, the one or more optical elements comprising a focusing objective;
    measuring, by a monitoring device, the pulse length of the one or more laser pulses to detect the change in the pulse length, the monitoring device coupled to or disposed within the focusing objective;
    receiving, at a control computer, the measured pulse length from the monitoring device;
    determining, by the control computer, one or more laser parameters that compensate for the change in the pulse length, the one or more laser parameters comprising a cycle number of the amplifier; and
    controlling, by the control computer, the laser source according to the one or more laser parameters by instructing the laser source to adjust the cycle number to compensate for the detected change in the pulse length.

8. The method of claim 7, wherein the change in the pulse length is an increase or decrease in pulse length.

9. The method of claim 7, the determining the one or more laser parameters comprises determining one or more parameters that introduce a positive or negative chirp to compensate for the change in pulse length.

10. The method of claim 7, wherein:
the one or more optical elements change the pulse length by causing a negative chirp in the laser pulses; and
the determining the one or more laser parameters comprises determining one or more parameters that introduce a positive chirp to compensate for the change in the pulse length.

11. The method of claim 7, the one or more laser parameters substantially compensate for the change in pulse length.

12. The method of claim 7, the one or more laser parameters partially compensate for the change in pulse length.

* * * * *